(12) United States Patent
Cole et al.

(10) Patent No.: US 7,868,004 B2
(45) Date of Patent: Jan. 11, 2011

(54) MENTHANE CARBOXAMIDE DERIVATIVES HAVING COOLING PROPERTIES

(75) Inventors: Lucienne Cole, Cincinnati, OH (US); Stefan Michael Furrer, Cincinnati, OH (US); Christophe C. Galopin, Chesterfield, VA (US); Pablo Victor Krawec, Cincinnati, OH (US); Adam Mazur, Mason, OH (US); Jay Patrick Slack, Loveland, OH (US)

(73) Assignee: Givaudan S.A., Vernier (CH)

( * ) Notice: Subject to any disclaimer, the term of this patent is extended or adjusted under 35 U.S.C. 154(b) by 477 days.

(21) Appl. No.: 11/884,479

(22) PCT Filed: Feb. 23, 2006

(86) PCT No.: PCT/CH2006/000116

§ 371 (c)(1),
(2), (4) Date: Dec. 19, 2007

(87) PCT Pub. No.: WO2006/092074

PCT Pub. Date: Sep. 8, 2006

(65) Prior Publication Data

US 2008/0305051 A1  Dec. 11, 2008

Related U.S. Application Data

(60) Provisional application No. 60/657,562, filed on Mar. 1, 2005.

(51) Int. Cl.
| | | |
|---|---|---|
| *A61K 31/535* | (2006.01) | |
| *A61K 31/425* | (2006.01) | |
| *A61K 31/42* | (2006.01) | |
| *A61K 31/41* | (2006.01) | |
| *A61K 31/415* | (2006.01) | |
| *A61K 31/36* | (2006.01) | |
| *C07D 277/62* | (2006.01) | |
| *C07D 263/54* | (2006.01) | |
| *C07D 249/08* | (2006.01) | |
| *C07D 231/56* | (2006.01) | |
| *C07D 295/12* | (2006.01) | |
| *C07D 295/22* | (2006.01) | |

(52) U.S. Cl. ............ 514/239.5; 514/367; 514/375; 514/383; 514/406; 514/464; 548/178; 548/217; 548/262.4; 548/361.1; 544/166; 549/434

(58) Field of Classification Search .......... 514/239.5, 514/367, 375, 383, 406, 464; 548/178, 217, 548/262.4, 361.1; 544/166; 549/434
See application file for complete search history.

(56) References Cited

U.S. PATENT DOCUMENTS

| | | |
|---|---|---|
| 2006/0051301 A1 | 3/2006 | Galopin et al. |
| 2006/0276667 A1 | 12/2006 | Galopin et al. |

FOREIGN PATENT DOCUMENTS

| | | |
|---|---|---|
| GB | 1 351 761 A | 5/1974 |
| WO | WO 2005/002582 A | 1/2005 |
| WO | WO 2005/020897 A | 3/2005 |
| WO | WO 2006/056087 A1 | 6/2006 |

*Primary Examiner*—Rebecca L Anderson
(74) *Attorney, Agent, or Firm*—Curatolo Sidoti Co., LPA; Joseph G. Curatolo; Salvatore A. Sidoti

(57) ABSTRACT

A compound of the formula I

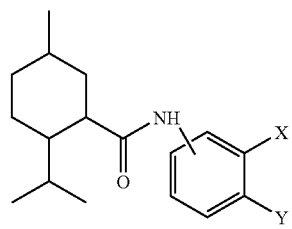

in which X and Y are selected as follows:
(i) X is H and Y is selected from the group consisting of

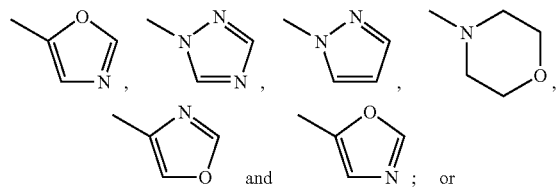

(ii) X and Y together form a bivalent radical selected from the group consisting of —O—CH$_2$—O—, —N═CH—O— and —N═CH—S— thus forming together with the carbon atoms to which the radical is attached a 5-membered ring.

The compounds have cooling properties and are useful in, for example, foodstuffs, dentifrices and cosmetics.

7 Claims, No Drawings

MENTHANE CARBOXAMIDE DERIVATIVES HAVING COOLING PROPERTIES

CROSS REFERENCE TO RELATED APPLICATIONS

This application is a national stage application of International Application No. PCT/CH2006/000116, filed 23 Feb. 2006, which claims the benefit of U.S. Provisional Patent Application No. 60/657,562, filed 1 Mar. 2005, from which applications priority is claimed, and which applications are hereby incorporated by reference herein as if fully written out below.

This invention relates to heterocyclic compounds having cooling properties.

Cooling compounds, that is, chemical compounds that impart a cooling sensation to the skin or the mucous membranes of the body, are well known to the art and are widely used in a variety of products such as foodstuffs, tobacco products, beverages, dentifrices, mouthwashes and toiletries.

One class of cooling compounds that have enjoyed substantial success consists of N-substituted p-menthane carboxamides. Examples of these compounds are described in, for example, British Patents GB 1,351,761-2 and U.S. Pat. No. 4,150,052.

It has now been found that a particular selection of such compounds exhibits a cooling effect that is both surprisingly strong and long-lasting. The invention therefore provides a compound of the formula I

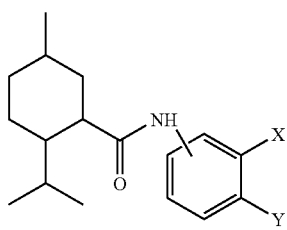

I in which X and Y are selected as follows:
(i) X is H and Y is selected from the group consisting of

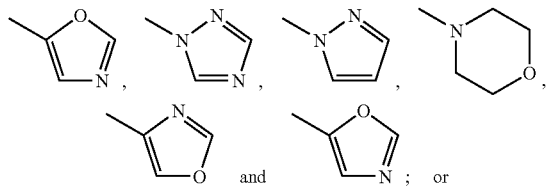

and          ; or (ii) X and Y together form a bivalent radical selected from the group consisting of —O—CH$_2$—O—, —N=CH—O— and —N=CH—S— thus forming together with the carbon atoms to which the radical is attached a 5-membered ring (a 1,3-dioxolane ring, a 1,3-oxazole ring or a 1,3-thiazole ring respectively)

Specific examples of compounds of Formula I are shown below:

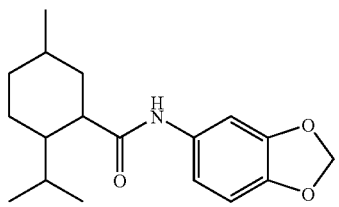

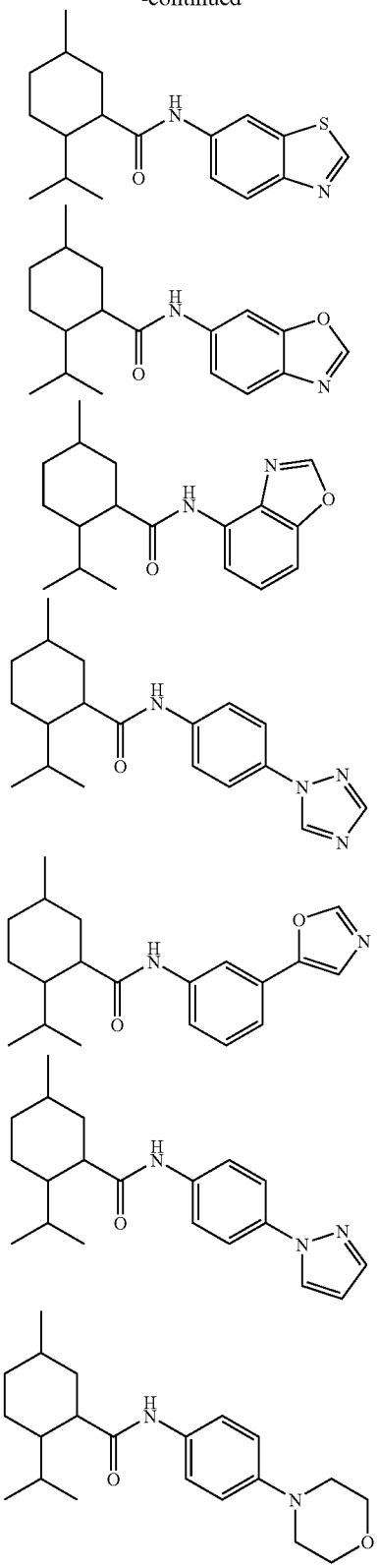

The compounds may be easily prepared and isolated by art-recognized methods

They are distinguished from similar compounds of the prior art by their surprisingly high cooling effect (up to 100 times higher than that of similar known compounds) and by the longevity of the cooling effect, which adds to their attractiveness in a large variety of products.

For example, a small group of panelists was asked to taste various solutions of cooling compounds and indicate which solutions had a cooling intensity similar or slightly higher than that of a solution of menthol at 2 ppm. Results are shown in table 1.

TABLE 1 experiment on cooling intensity.

| Chemical | Concentration |
| --- | --- |
| l-Menthol | 2.0 ppm |
| N-4-(pyrazol-1-yl)-phenyl-3-p-menthanecarboxamide | 0.02 ppm |
| N-4-([1,2,4]triazol-1-yl)-phenyl-3-p-menthanecarboxamide | 0.02 ppm |
| N-3-(oxazol-5-yl)-phenyl-3-p-menthanecarboxamide | 0.1 ppm |
| N-4-(morpholin-4-yl)-phenyl 3-p-menthanecarboxamide | 0.2 ppm |
| N-4-(oxazol-5-yl)-phenyl-3-p-menthanecarboxamide | 0.5 ppm |
| N-benzooxazol-4-yl-3-p-menthanecarboxamide | 0.02 ppm |
| N-benzo[1,3]dioxol-5-yl-3-p-menthanecarboxamide | 0.02 ppm |
| N-benzothiazol-6-yl menthanecarboxamide | 0.3 ppm |

From Table 1, it can be seen that the compounds of Formula I are up to 100 times stronger than menthol, the reference cooling compound. Compounds of Formula I are also much stronger and last longer than WS-3, the best cooling compound of the prior art.

The compounds of the invention may be used in products that are applied to the mouth or the skin to give a cooling sensation. By "applying" is meant any form of bringing into contact, for example, oral ingestion or, in the case of tobacco products, inhalation. In the case of application to the skin, it may be, for example, by including the compound in a cream or salve, or in a sprayable composition. The invention therefore also provides a method of providing a cooling effect to the mouth or skin by applying thereto a product comprising a compound as hereinabove described. The invention also provides a composition that provides a cooling sensation to the skin or oral cavity, comprising a compound as hereinabove defined.

The invention is now further described by means of the following non-limiting examples, which describe preferred embodiments.

EXAMPLE 1

Preparation of N-benzooxazol-4-yl 3-p-menthanecarboxamide

To a flask, were added 0.5 g (3.7 mmol) of benzooxazol-4-ylamine, 0.7 mL of triethylamine and 10 mL of dichloromethane. The mixture is cooled to 0° C. and 0.71 g of 3-p-menthanecarboxyl chloride were added dropwise over 5 minutes. The reaction mixture was stirred overnight. To the reaction mixture, 10 mL of water were added. The mixture was separated. The aqueous layer is washed with EtOAc (3×5 mL). The combined organic layers were washed with 5 mL water. The organic layer was dried over $Na_2SO_4$. The solvent was evaporated in vacuo to afford the crude product, which was purified over silica gel to afford 0.46 g of the desired product with the following spectroscopic properties:

MS: 300 ([M$^+$]), 133, 97, 83

$^1$H NMR (300 MHz; CDCl$_3$) δ: 8.35 (s, 1H), 8.14 (d, 1H), 7.68 (d, 1H), 7.54 (br. s, 1H), 7.18 (dd, 1H), 2.25 (t, 1H), 1.91-1.61 (m, 5H), 1.5-1.23 (m, 2H), 1.17-0.9 (m, 2H), 0.94 (d, 3H), 0.93 (d, 3H), 0.85 (d, 3H)

EXAMPLE 2

Preparation of N-benzooxazol-6-yl 3-p-menthanecarboxamide

A preparation similar to that described in example 1 gives the desired product with the following spectroscopic properties:

MS: 300 ([M$^+$]), 133, 97, 83

$^1$H NMR (300 MHz; CD3OD) δ: 8.33 (s, 1H), 8.02 (m, 2H), 7.23 (dd, 1H), 2.4 (ddd, 1H), 1.88-1.54 (m, 5H), 1.37 (m, 1H), 1.0-1.3 (m, 3H), 0.98 (d, 3H), 0.86 (d, 3H), 0.82 (d, 3H)

EXAMPLE 3

Preparation of N-benzothiazol-6-yl menthanecarboxamide

A preparation similar to that described in example 1 gives the desired product with the following spectroscopic properties:

MS: 316 ([M$^+$]), 150, 97, 83

$^1$H NMR (300 MHz; CD3OD) δ: 9.12 (s, 1H), 8.49 (d, 1H), 7.91 (d, 1H), 7.54 (d, 1H), 2.2 (ddd, 1H), 1.88-1.54 (m, 5H), 1.21-1.47 (m, 4H), 0.99 (d, 3H), 0.93 (d, 3H), 0.85 (d, 3H)

EXAMPLE 4

Preparation of N-4-([1,2,4]triazol-1-yl)-phenyl-3-p-menthanecarboxamide

A preparation similar to that described in example 1 gives the desired product with the following spectroscopic properties:

MS: 326 ([M$^+$]), 160, 97, 83

$^1$H NMR (300 MHz; CD3OD) δ: 8.98 (s, 1H), 8.07 (s, 1H), 7.84 (s, 4H), 2.26 (t, 1H), 1.9-1.5 (m, 5H), 1.45-1.3 (m, 1H), 1.25-1 (m, 3H), 0.94 (d, 3H), 0.86 (d, 3H), 0.8 (d, 3H)

EXAMPLE 5

Preparation of N-4-(oxazol-5-yl)-phenyl-3-p-menthanecarboxamide

A preparation similar to that described in example 1 gives the desired product with the following spectroscopic properties:

MS: 326 ([M$^+$]), 160, 139, 97, 83

$^1$H NMR (300 MHz; CD3OD) δ: 8.19 (s, 1H), 7.66 (s, 4H), 7.42 (s, 1H), 2.35 (ddd, 1H), 1.88-1.54 (m, 5H), 1.4-1.35 (m, 1H), 1.0-1.3 (m, 3H), 0.95 (d, 3H), 0.91 (d, 3H), 0.84 (d, 3H)

EXAMPLE 6

Preparation of N-3-(oxazol-5-yl)-phenyl-3-p-menthanecarboxamide

A preparation similar to that described in example 1 gives the desired product with the following spectroscopic properties:

MS: 326 ([M$^+$]), 160, 139, 97, 83

EXAMPLE 7

Application in Mouthwash

| | |
|---|---|
| Alcohol 95% | 177 mL |
| Sorbitol 70% | 290 g |
| Compound of example 1 as a 1% solution in alcohol | 10 mL |
| Peppermint oil, Terpeneless | 0.300 g |
| Methyl salicylate | 0.640 g |
| Eucalyptol | 0.922 g |
| Thymol | 0.639 g |
| Benzoic acid | 1.500 g |
| Pluronic F127 | 5.000 g |
| Sodium Saccharin | 0.600 g |
| Sodium Citrate | 0.300 g |
| Citric Acid | 0.100 g |
| Water | q.s. 1 liter |

All the ingredients are mixed. 30 mL of obtained solution is put in the mouth, swished around, gargled and spit out. An intense cooling is felt in every area of the mouth as well as lips. The cooling perception lasts for several hours

EXAMPLE 8

Application in Toothpaste

| | |
|---|---|
| Opaque toothgel | 98.000 g |
| Compound of example 6 as a 2% solution in PG | 1.500 g |
| Peppermint oil, Terpeneless | 0.500 g |

The chemicals are mixed in the toothgel, a piece of toothgel is put on a toothbrush and a panelist's teeth are brushed. The mouth is rinsed with water and the water is spit out. An intense cooling sensation is felt by the panelist in all areas of the mouth. The cooling perception lasts for several hours.

The invention claimed is:

1. A compound of formula I

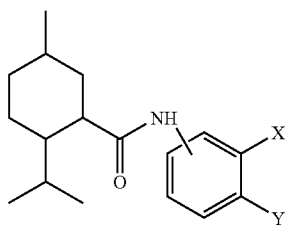

I in which X and Y are selected as follows:
   (i) X is H and Y is selected from the group consisting of

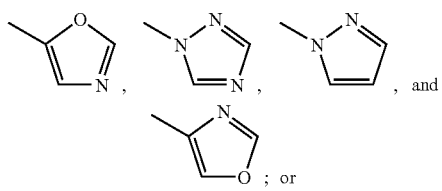

, and

; or (ii) X and Y together form a bivalent radical selected from the group consisting of, —N=CH—O— and —N=CH—S—, thus forming together with the carbon atoms to which the radical is attached a 5-membered ring.

2. A method of providing a cooling effect to the mouth or skin by applying thereto a product comprising the compound according to claim 1.

3. A composition that provides a cooling sensation to the skin or oral cavity, comprising the compound according to claim 1.

4. The compound of claim 1, selected from the group consisting of

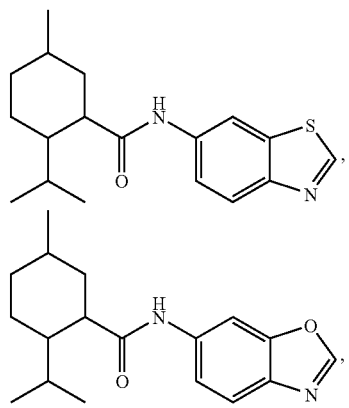

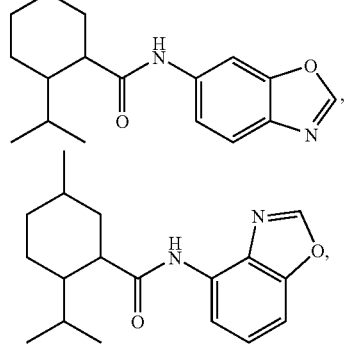

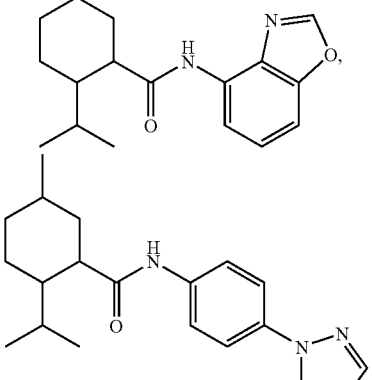

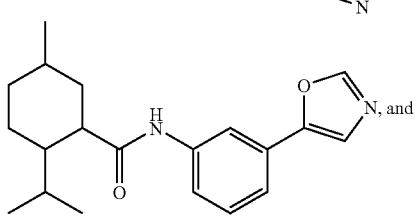

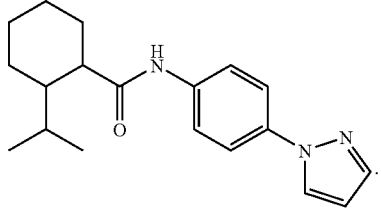

5. The method according to claim 2, wherein the compound is selected from the group consisting of

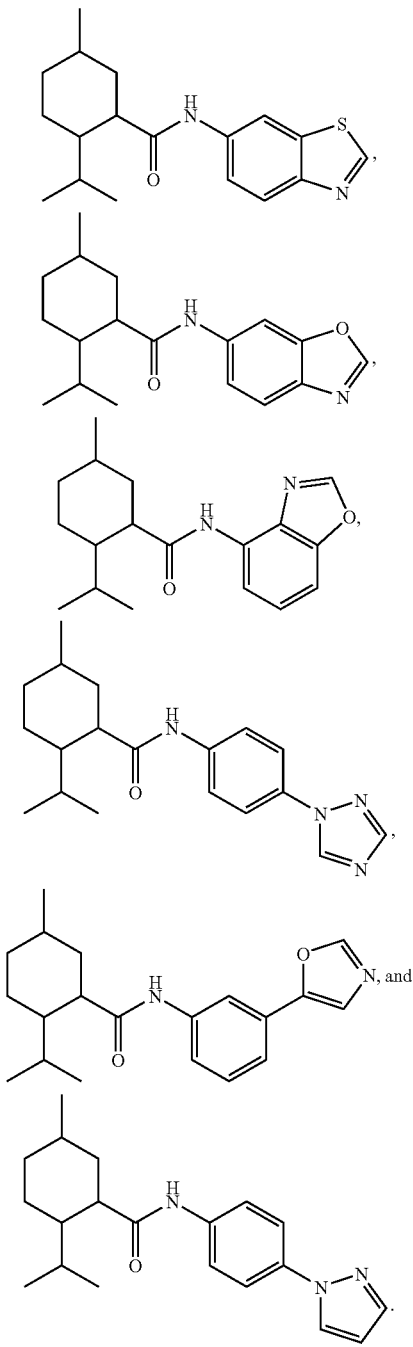

6. The method according to claim 2, wherein the product comprises an orally ingestible foodstuff or beverage, a tobacco product, a cream, a salve, a sprayable composition, a mouthwash, a toothpaste, a dentifrice, or a toiletry.

7. The composition of claim 3 wherein the compound is selected from the group consisting of

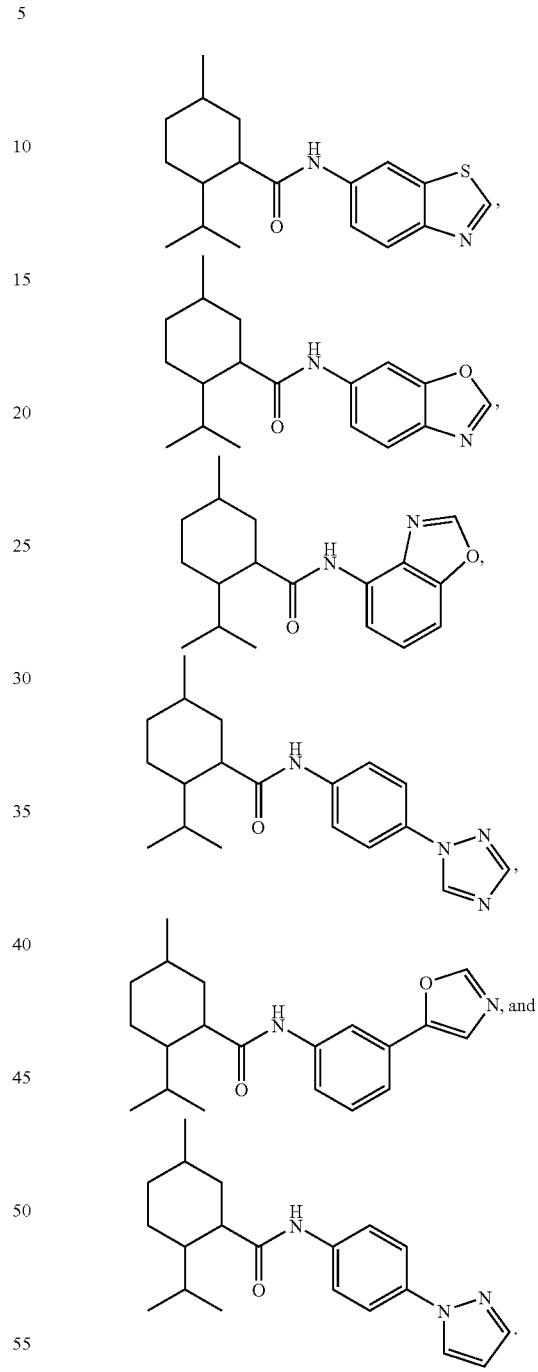

* * * * *